(12) United States Patent
Bonnert (10) Patent No.: US 7,179,898 B1
(45) Date of Patent: Feb. 20, 2007

(54) HUMAN VANILLOID RECEPTOR-LIKE RECEPTOR

(75) Inventor: Timothy Peter Bonnert, Much Hadham (GB)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/445,614

(22) Filed: Dec. 8, 1999

(30) Foreign Application Priority Data

Dec. 8, 1998 (GB) ................... 9827016.8

(51) Int. Cl.
 *C07H 21/04* (2006.01)
 *C12N 15/63* (2006.01)
 *C12N 15/12* (2006.01)
 *C12N 1/15* (2006.01)

(52) U.S. Cl. .................. 536/23.5; 435/6; 435/7.21; 435/69.1; 435/252.3; 435/325; 436/501; 530/300; 530/350; 514/2

(58) Field of Classification Search ............... 530/350; 435/6, 7.1, 7.21, 69.5, 252.3; 436/501; 536/23.5
 See application file for complete search history.

(56) References Cited

U.S. PATENT DOCUMENTS

| | | | | |
|---|---|---|---|---|
| 5,834,183 A | * | 11/1998 | Orr et al. ................. | 435/6 |
| 6,335,180 B1 | * | 1/2002 | Julius et al. | |
| 6,444,440 B1 | * | 9/2002 | Young et al. ............. | 435/69.1 |

2005/0158827 A1 * 7/2005 Curtis

FOREIGN PATENT DOCUMENTS

| | | |
|---|---|---|
| EP | A 0953638 | 3/1999 |
| EP | 1 160 254 A1 | 5/2001 |
| WO | WO 99/09140 | 2/1999 |
| WO | WO 00 99/37765 | 7/1999 |
| WO | WO 99/37675 | 7/1999 |
| WO | WO 99/46377 | 9/1999 |
| WO | WO 00/22121 | 4/2000 |
| WO | WO 00/29577 | 5/2000 |
| WO | WO 00/32766 | 6/2000 |

OTHER PUBLICATIONS

Bowie et al., Science 247 (1306)1990.*
SIGMA Product Catalogue, p. 743, 1992.*
Caterina et al., Nature 398(436)1999.*
Sambrook et al., Molecular Cloning, 1989, p. C.10.*
Caterina, M. J., Schumacher, M. A., Tominaga, M., Rosen, T. A., Levine, J. D. & Julius, D The capsaicin receptor: a heat-activated ion channel in the pain pathway, Nature, Oct. 23, 1997, pp. 816-824, vol. 389.
Caterina, M. J. et al. "A capsaicin-receptor homologue with a high threshold for noxious heat", Nature, 1999, vol. 398, pp. 436-441.

* cited by examiner

*Primary Examiner*—Janet L. Andres
*Assistant Examiner*—Michael Brannock
(74) *Attorney, Agent, or Firm*—Jack L. Tribble; Patricia L. Chisholm (57) ABSTRACT

The present invention discloses a human vanilloid receptor-like (VR-L) receptor.

6 Claims, 4 Drawing Sheets

CACGAGGCCGACGCGCAGCTGGGAGGAAGACAGGACCCTTGACATCTCCATCTGCACAGA

GGTCCTGGCTGGACCGAGCAGCCTCCTCCTCCTAGGATGACCTCACCCTCCAGCTCTCCA
                                        M  T  S  P  S  S  S  P

GTTTTCAGGTTGGAGACATTAGATGGAGGCCAAGAAGATGGCTCTGAGGCGGACAGAGGA
V  F  R  L  E  T  L  D  G  G  Q  E  D  G  S  E  A  D  R  G

AAGCTGGATTTTGGGAGCGGGCTGCCTCCCATGGAGTCACAGTTCCAGGGCGAGGACCGG
K  L  D  F  G  S  G  L  P  P  M  E  S  Q  F  Q  G  E  D  R

AAATTCGCCCCTCAGATAAGAGTCAACCTCAACTACCGAAAGGGAACAGGTGCCAGTCAG
K  F  A  P  Q  I  R  V  N  L  N  Y  R  K  G  T  G  A  S  Q

CCGGATCCAAACCGATTTGACCGAGATCGGCTCTTCAATGCGGTCTCCCGGGGTGTCCCC
P  D  P  N  R  F  D  R  D  R  L  F  N  A  V  S  R  G  V  P

GAGGATCTGGCTGGACTTCCAGAGTACCTGAGCAAGACCAGCAAGTACCTCACCGACTCG
E  D  L  A  G  L  P  E  Y  L  S  K  T  S  K  Y  L  T  D  S

GAATACACAGAGGGCTCCACAGGTAAGACGTGCCTGATGAAGGCTGTGCTGAACCTTAAG
E  Y  T  E  G  S  T  G  K  T  C  L  M  K  A  V  L  N  L  K

GACGGAGTCAATGCCTGCATTCTGCCACTGCTGCAGATCGACAGGGACTCTGGCAATCCT
D  G  V  N  A  C  I  L  P  L  L  Q  I  D  R  D  S  G  N  P

CAGCCCCTGGTAAATGCCCAGTGCACAGATGACTATTACCGAGGCCACAGCGCTCTGCAC
Q  P  L  V  N  A  Q  C  T  D  D  Y  Y  R  G  H  S  A  L  H

ATCGCCATTGAGAAGAGGAGTCTGCAGTGTGTGAAGCTCCTGGTGGAGAATGGGGCCAAT
I  A  I  E  K  R  S  L  Q  C  V  K  L  L  V  E  N  G  A  N

GTGCATGCCCGGGCCTGCGGCCGCTTCTTCCAGAAGGGCCAAGGGACTTGCTTTTATTTC
V  H  A  R  A  C  G  R  F  F  Q  K  G  Q  G  T  C  F  Y  F

GGTGAGCTACCCCTCTCTTTGGCCGCTTGCACCAAGCAGTGGGATGTGGTAAGCTACCTC
G  E  L  P  L  S  L  A  A  C  T  K  Q  W  D  V  V  S  Y  L

CTGGAGAACCCACACCAGCCCGCCAGCCTGCAGGCCACTGACTCCCAGGGCAACACAGTC
L  E  N  P  H  Q  P  A  S  L  Q  A  T  D  S  Q  G  N  T  V

CTGCATGCCCTAGTGATGATCTCGGACAACTCAGCTGAGAACATTGCACTGGTGACCAGC
L  H  A  L  V  M  I  S  D  N  S  A  E  N  I  A  L  V  T  S

ATGTATGATGGGCTCCTCCAAGCTGGGGCCCGCCTCTGCCCTACCGTGCAGCTTGAGGAC
M  Y  D  G  L  L  Q  A  G  A  R  L  C  P  T  V  Q  L  E  D

ATCCGCAACCTGCAGGATCTCACGCCTCTGAAGCTGGCCGCCAAGGAGGGCAAGATCGAG
I  R  N  L  Q  D  L  T  P  L  K  L  A  A  K  E  G  K  I  E

ATTTTCAGGCACATCCTGCAGCGGGAGTTTTCAGGACTGAGCCACCTTTCCCGAAAGTTC
I  F  R  H  I  L  Q  R  E  F  S  G  L  S  H  L  S  R  K  F

ACCGAGTGGTGCTATGGGCCTGTCCGGGTGTCGCTGTATGACCTGGCTTCTGTGGACAGC
T  E  W  C  Y  G  P  V  R  V  S  L  Y  D  L  A  S  V  D  S

TGTGAGGAGAACTCAGTGCTGGAGATCATTGCCTTTCATTGCAAGAGCCCGCACCGACAC
C  E  E  N  S  V  L  E  I  I  A  F  H  C  K  S  P  H  R  H

CGAATGGTCGTTTTGGAGCCCCTGAACAAACTGCTGCAGGCGAAATGGGATCTGCTCATC
R  M  V  V  L  E  P  L  N  K  L  L  Q  A  K  W  D  L  L  I

CCCAAGTTCTTCTTAAACTTCCTGTGTAATCTGATCTACATGTTCATCTTCACCGCTGTT

GCCTACCATCAGCCTACCCTGAAGAAGCAGGCCGCCCCTCACCTGAAAGCGGAGGTTGGA
 A  Y  H  Q  P  T  L  K  K  Q  A  A  P  H  L  K  A  E  V  G

AACTCCATGCTGCTGACGGGCCACATCCTTATCCTGCTAGGGGGGATCTACCTCCTCGTG
 N  S  M  L  L  T  G  H  I  L  I  L  L  G  G  I  Y  L  L  V

GGCCAGCTGTGGTACTTCTGGCGGCGCCACGTGTTCATCTGGATCTCGTTCATAGACAGC
 G  Q  L  W  Y  F  W  R  R  H  V  F  I  W  I  S  F  I  D  S

TACTTTGAAATCCTCTTCCTGTTCCAGGCCCTGCTCACAGTGGTGTCCCAGGTGCTGTGT
 Y  F  E  I  L  F  L  F  Q  A  L  L  T  V  V  S  Q  V  L  C

TTCCTGGCCATCGAGTGGTACCTGCCCCTGCTTGTGTCTGCGCTGGTGCTGGGCTGGCTG
 F  L  A  I  E  W  Y  L  P  L  L  V  S  A  L  V  L  G  W  L

AACCTGCTTTACTATACACGTGGCTTCCAGCACACAGGCATCTACAGTGTCATGATCCAG
 N  L  L  Y  Y  T  R  G  F  Q  H  T  G  I  Y  S  V  M  I  Q

AAGGTCATCCTGCGGGACCTGCTGCGCTTCCTTCTGATCTACTTAGTCTTCCTTTTCGGC
 K  V  I  L  R  D  L  L  R  F  L  L  I  Y  L  V  F  L  F  G

TTCGCTGTAGCCCTGGTGAGCCTGAGCCAGGAGGCTTGGCGCCCCGAAGCTCCTACAGGC
 F  A  V  A  L  V  S  L  S  Q  E  A  W  R  P  E  A  P  T  G

CCCAATGCCACAGAGTCAGTGCAGCCCATGGAGGGACAGGAGGACGAGGGCAACGGGGCC
 P  N  A  T  E  S  V  Q  P  M  E  G  Q  E  D  E  G  N  G  A

CAGTACAGGGGTATCCTGGAAGCCTCCTTGGAGCTCTTCAAATTCACCATCGGCATGGGC
 Q  Y  R  G  I  L  E  A  S  L  E  L  F  K  F  T  I  G  M  G

GAGCTGGCCTTCCAGGAGCAGCTGCACTTCCGCGGCATGGTGCTGCTGCTGCTGCTGGCC
 E  L  A  F  Q  E  Q  L  H  F  R  G  M  V  L  L  L  L  L  A

TACGTGCTGCTCACCTACATCCTGCTGCTCAACATGCTCATCGCCCTCATGAGCGAGACC
 Y  V  L  L  T  Y  I  L  L  L  N  M  L  I  A  L  M  S  E  T

GTCAACAGTGTCGCCACTGACAGCTGGAGCATCTGGAAGCTGCAGAAAGCCATCTCTGTC
 V  N  S  V  A  T  D  S  W  S  I  W  K  L  Q  K  A  I  S  V

CTGGAGATGGAGAATGGCTATTGGTGGTGCAGGAAGAAGCAGCGGGCAGGTGTGATGCTG
 L  E  M  E  N  G  Y  W  W  C  R  K  K  Q  R  A  G  V  M  L

ACCGTTGGCACTAAGCCAGATGGCAGCCCGGATGAGCGCTGGTGCTTCAGGGTGGAGGAG
 T  V  G  T  K  P  D  G  S  P  D  E  R  W  C  F  R  V  E  E

GTGAACTGGGCTTCATGGGAGCAGACGCTGCCTACGCTGTGTGAGGACCCGTCAGGGGCA
 V  N  W  A  S  W  E  Q  T  L  P  T  L  C  E  D  P  S  G  A

GGTGTCCCTCGAACTCTCGAGAACCCTGTCCTGGCTTCCCCTCCCAAGGAGGATGAGGAT
 G  V  P  R  T  L  E  N  P  V  L  A  S  P  P  K  E  D  D

GGTGCCTCTGAGGAAAACTATGTGCCCGTCCAGCTCCTCCAGTCCAACTGATGGCCCAGA
 G  A  S  E  E  N  Y  V  P  V  Q  L  L  Q  S  N  *

TGCAGCAGGAGGCCAGAGGACAGAGCAGAGGATCTTTCCAACCACATCTGCTGGCTCTGG

GGTCCCAGT
```

```
104F    CAG GCC CGG GCA TGC ACA TTG
105T    CCA GGG CGA GGA CCG GAA ATT
108F    GAC AGC TGG AGC ATC TGG AAG
109F    GAC AGC TGG AGC ATC TGG AAG
110T    CTT CCA GAT GCT CCA GCT GTC
111T    TTT GCC ACC AGA ATT CAC TGG
114F    CTC TCT TTG GCC GCT TGC ACC
115T    CCA GCA CTG AGT TCT CCT CAC
118F    GCC CTA CCG TGC AGC TTG AGG
119T    TGC CCC ACG AGG AGG TAG ATC
120F    ATG GCG ATG TGC AGA GCG CTG
121T    AGA GTC AAC CTC AAA CTA CCG
126F    GAG CTT CTC CCT GCG GTC AAG
127T    AAG GCT GCT GAA AAA GCA CTG
189F    GCT GGG CTG GCT GAA CCT GC
190T    GAG GGC AAT GAG CAT GTT G
```

FIG. 3

HUMAN VANILLOID RECEPTOR-LIKE RECEPTOR

This application claims priority to GB Application No. 9827016.8, filed Dec. 8, 1998, now abandoned.

The present invention is in the field of molecular biology; more particularly, the present invention relates to a nucleic acid sequence and an amino acid sequence for a novel human vanilloid receptor-like receptor (VR-L). The invention further relates to a stable cell line expressing a VR-L receptor and the use of the cell line in a screening technique for the design and development of receptor specific medicaments.

The present invention provides a unique nucleotide sequence which encodes a novel human vanilloid receptor-like (VR-L) receptor. The cDNA, hereinafter designated vr-l, was identified and cloned using IMAGE clones 1286108 and 705190 from human tonsillar cells enriched for germinal centre B cells.

The invention relates to the use of nucleic acid and amino acid sequences of VR-L or its variants, in the diagnosis or treatment of activated, inflamed or diseased cells and/or tissues associated with its expression. Aspects of the invention include the antisense DNA or vr-l; cloning or expression vectors containing vr-l; host cells or organisms transformed with expression vectors containing vr-l; a method for the production and recovery of purified VR-L from host cells; and purified protein, VR-L, which can be used to identify inhibitors for the down regulation of signal transduction involving VR-L.

BRIEF DESCRIPTION OF THE DRAWINGS

FIGS. 1A–1B show the nucleic acid sequence (coding region of SEQ ID NO: 1) and the predicted amino acid sequence (SEQ ID NO:2) for VR-L.

DETAILED DESCRIPTION

As used herein and designated by the upper case abbreviation, VR-L, refers to a vanilloid receptor-like receptor homologue in either naturally occurring or synthetic form and active fragments thereof which have the amino acid sequence of SEQ ID NO:2. In one embodiment, the polypeptide VR-L is encoded by mRNAs transcribed from the cDNA, as designated by the lower case abbreviation, vr-l, of SEQ ID NO:1.

The novel human vanilloid receptor-like receptor VR-L, which is the subject of this patent application, was discovered among the partial cDNA sequences present in the EST database and the corresponding IMAGE clones.

An "oligonucleotide" is a stretch of nucleotide residues which has a sufficient number of bases to be used as an oligomer, amplimer or probe in a polymerase chain reaction (PCR). Oligonucleotides are usually prepared by chemical synthesis. Their sequence is based on cDNA or genomic sequence information and are used to amplify, reveal or confirm the presence of a similar DNA or RNA in a particular cell or tissue. Oligonucleotides or oligomers comprise portions of a DNA sequence having at least about 10 nucleotides and as many as about 35 nucleotides, preferably about 25 nucleotides.

"Probes" may be derived from naturally occurring or recombinant single- or double-stranded nucleic acids or be chemically synthesised. They are useful in detecting the presence of identical or similar sequences.

A "portion" or "fragment" of a polynucleotide or nucleic acid comprises all or part of the nucleotide sequence having fewer nucleotides than about 6 kb, preferably fewer than about 1 kb which can be used as a probe. Such probes may be labelled with reporter molecules using nick translation, Klenow fill-in reaction, PCR or other methods well known in the art. After pre-testing to optimise reaction conditions and to eliminate false positives, nucleic acid probes may be used in Southern, Northern or in situ hybridizations to determine whether DNA or RNA encoding VR-L is present in a cell type, tissue, or organ.

"Reporter" molecules are those radionuclides, enzymes, fluorescent, chemiluminescent, or chromogenic agents which associate with, establish the presence of, and may allow quantification of a particular nucleotide or amino acid sequence.

"Recombinant nucleotide variants" encoding VR-L may be synthesised by making use of the "redundancy" in the genetic code. Various codon substitutions, such as the silent changes which produce specific restriction sites or codon usage-specific mutations, may be introduced to optimise cloning into a plasmid or viral vector or expression in a particular prokaryotic or eukaryotic host system, respectively.

"Chimeric" molecules may be constructed by introducing all or part of the nucleotide sequence of this invention into a vector containing additional nucleic acid sequence which might be expected to change any one (or more than one) of the following VR-L characteristics: cellular location, distribution, ligand-binding affinities, interchain affinities, degradation/turnover rate, signalling, etc.

"Active" refers to those forms, fragments, or domains of any VR-L polypeptide which retain the biological and/or antigenic activities of any naturally occurring VR-L.

"Naturally occurring VR-L" refers to a polypeptide produced by cells which have not been genetically engineered and specifically contemplates various polypeptides arising from post-translational modifications of the polypeptide including but not limited to acetylation, carboxylation, glycosylation, phosphorylation, lipidation and acylation.

"Derivative" refers to those polypeptides which have been chemically modified by such techniques as ubiquitination, labelling (see above), pegylation (derivatization with polyethylene glycol), and chemical insertion or substitution of amino acids such as ornithine which do not normally occur in human proteins.

"Recombinant polypeptide variant" refers to any polypeptide which differs from naturally occurring VR-L by amino acid insertions, deletions and/or substitutions, created using recombinant DNA techniques. Guidance in determining which amino acid residues may be replaced, added or deleted without abolishing activities or interest may be found by comparing the sequence of VR-L with that of related polypeptides and minimizing the number of amino acid sequence changes made in highly conserved regions.

Amino acid "substitutions" are conservative in nature when they result from replacing one amino acid with another having similar structural and/or chemical properties, such as the replacement of a leucine with an isoleucine or valine, an aspartate with a glutamate, or a threonine with a serine.

"Insertions" or "deletions" are typically in the range of about 1 to 5 amino acids. The variation allowed may be experimentally determined by producing the peptide synthetically or by systematically making insertions, deletions, or substitutions of nucleotides in the vr-l sequence using recombinant DNA techniques.

An "oligopeptide" is a short stretch of amino acid residues and may be expressed from an oligonucleotide. It may be functionally equivalent to and the same length as (or considerably shorter than) a "fragment", "portion", or "segment" of a polypeptide. Such sequences comprise a stretch of amino acid residues of at least about 5 amino acids and often about 17 or more amino acids, typically at least about 9 to 13 amino acids, and of sufficient length to display biological and/or antigenic activity.

"Inhibitor" is any substance which retards or prevents a chemical or physiological reaction or response. Common inhibitors include but are not limited to antisense molecules, antibodies, and antagonists.

"Standard" expression is a quantitative or qualitative measurement for comparison. It is based on a statistically appropriate number of normal samples and is created to use as a basis of comparison when performing diagnostic assays, running clinical trials, or following patient treatment profiles.

The present invention provides a nucleotide sequence uniquely identifying a novel human vanilloid receptor-like receptor. Because the receptor is responsive to heat, the nucleic acids (vr-l), polypeptides (VR-L) and antibodies to VR-L are useful in diagnostic assays which survey for increased receptor production or function. A diagnostic test for excessive expression of VR-L can accelerate diagnosis and proper treatment of abnormal conditions associated with pain.

The nucleotide sequences encoding VR-L (or their complement) have numerous applications in techniques known to those skilled in the art of molecular biology. These techniques include use as hybridization probes, use in the construction of oligomers for PCR, use for chromosome and gene mapping, use in the recombinant production of VR-L, and use in generation of antisense DNA or RNA, their chemical analogues and the like. Uses of nucleotides encoding VR-L disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g. the triplet genetic code, specific base pair interactions, etc.

It will be appreciated by those skilled in the art that as a result of the degeneracy of the genetic code, a multitude of VR-L-encoding nucleotide sequences may be produced. Some of these will only bear minimal homology to the nucleotide sequence of the known and naturally occurring VR-L. The invention has specifically contemplated each and every possible variation of nucleotide sequence that could be made by selecting combinations based on possible codon choices. These combinations are made in accordance with the standard triplet genetic code as applied to the nucleotide sequence of naturally occurring vr-l, and all such variations are to be considered as being specifically disclosed. The variant given in FIG. 1 is preferred.

Although the nucleotide sequences which encode VR-L, its derivatives or its variants are preferably capable of hybridizing to the nucleotide sequence of the naturally occurring vr-l under stringent conditions, it may be advantageous to produce nucleotide sequences encoding VR-L or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding VR-L and/or its derivatives without altering the encoded aa sequence include the production of RNA transcripts having more desirable properties, such as a greater half-life, than transcripts produced from the naturally occurring sequence.

Nucleotide sequences encoding VR-L may be joined to a variety of other nucleotide sequences by means of well established recombinant DNA-techniques (Sambrook J et al (1989) Molecular Cloning: A Laboratory Manual, Cold Spring Harbor Laboratory, Cold Spring Harbor N.Y.; or Ausubel F M et al (1989) Current Protocols in Molecular Biology, John Wiley & Sons, New York City). Useful nucleotide sequences for joining to vr-l include an assortment of cloning vectors such as plasmids, cosmids, lambda phage derivatives, phagemids, and the like. Vectors of interest include expression vectors, replication vectors, probe generation vectors, sequencing vectors, etc. In general, vectors of interest may contain an origin of replication functional in at least one organism, convenient restriction endonuclease sensitive sites, and selectable markers for one or more host cell systems.

Another aspect of the subject invention is to provide for vr-l-specific hybridization probes capable of hybridizing with naturally occurring nucleotide sequences encoding VR-L. Such probes may also be used for the detection of similar sequences and should preferably contain at least 50% of the nucleotides from the vr-l sequence. The hybridization probes of the present invention may be derived from the nucleotide sequence presented as SEQ ID NO:1 or from genomic sequences including promoters, enhancers or introns of the native gene. Hybridization probes may be labeled by a variety of reporter molecules using techniques well known in the art.

PCR as described U.S. Pat. Nos. 4,683,195; 4,800,195; and 4,965,188 provides additional uses for oligonucleotides based upon the nucleotide sequence which encodes VR-L. Such probes used in PCR may be of recombinant origin, chemically synthesised, or a mixture of both. Oligomers may comprise discrete nucleotide sequences employed under optimised conditions for identification of vr-l in specific tissues or diagnostic use. The same two oligomers, a nested set of oligomers, or even a degenerate pool of oligomers may be employed under less stringent conditions for identification of closely related DNAs or RNAs.

Other means of producing specific hybridization probes for vr-l include the cloning of nucleic acid sequences encoding VR-L or VR-L derivatives into vectors for the production of mRNA probes. Such vectors are known in the art, are commercially available and may be used to synthesise RNA probes in vitro by means of the addition of the appropriate RNA polymerase as T7 or SP6 RNA polymerase and the appropriate reporter molecules.

It is possible to produce a DNA sequence, or portions thereof, entirely by synthetic chemistry. After synthesis, the nucleic acid sequence can be inserted into any of the many available DNA vectors and their respective host cells using techniques which are well known in the art. Moreover, synthetic chemistry may be used to introduce mutations into the nucleotide sequence. Alternatively, a portion of sequence in which a mutation is desired can be synthesised and recombined with longer portion of an existing genomic or recombinant sequence.

The nucleotide sequence for vr-l can be used in an assay to detect inflammation or disease associated with abnormal levels of VR-L expression. The cDNA can be labeled by methods known in the art, added to a fluid, cell or tissue sample from a patient, and incubated under hybridising conditions. After an incubation period, the sample is washed with a compatible fluid which contains a reporter molecule. After the compatible fluid is rinsed off, the reporter molecule is quantitated and compared with a standard as previously defined. If kinase expression is significantly different from standard expression, the assay indicates inflammation or disease.

The nucleotide sequence for vr-l can be used to construct hybridisation probes for mapping the native gene. The gene may be mapped to a particular chromosome or to a specific region of a chromosome using well known mapping techniques. These techniques include in situ hybridisation of chromosomal spreads (Verma et al (1988) Human Chromosomes: A Manual of Basic Techniques, Pergamon Press, New York City), flow-sorted chromosomal preparations, or artificial chromosome constructions such as yeast artificial chromosomes (YACs), bacterial artificial chromosomes (BACs), bacterial P1 constructions or single chromosome cDNA libraries.

In situ hybridisation of chromosomal preparations and physical mapping techniques such a linkage analysis using established chromosomal markers are invaluable in extending genetic maps. Examples of genetic map data can be found in the yearly genome issue of Science (eg 1994, 265:1981f). Often locating a gene on the chromosome of another mammalian species may reveal associated markers which can be used to help identify the analogous human chromosome.

New nucleotide sequences can be assigned to chromosomal subregions by physical mapping. The mapping of new genes or nucleotide sequences provide useful landmarks for investigators searching for disease genes using positional cloning or other gene discovery techniques. Once a disease or syndrome, such as ataxia telangiectasia (AT) has been crudely localised by genetic linkage to a particular genomic region, for example, AT to 11q22-23 (Gatti et al (1988) Nature 336:577–580), any sequences mapping to that area may represent or reveal genes for further investigation. The nucleotide sequence of the subject invention may also be used to detect differences in gene sequence between normal and carrier or affected individuals.

Nucleotide sequences encoding vr-l may be used to produce a purified oligo- or polypeptide using well known methods of recombinant DNA technology. Goeddel (1990, Gene Expression Technology, Methods and Enzymology, Vol 185, Academic Press, San Diego Calif.) is one among many publications which teach expression of an isolated nucleotide sequence. The oligopeptide may be expressed in a variety of host cells, either prokaryotic or eukaryotic. Host cells may be from the same species from which the nucleotide sequence was derived or from a different species. Advantages of producing an oligonucleotide by recombinant DNA technology include obtaining adequate amounts of the protein for purification and the availability of simplified purification procedures.

Cells transformed with DNA encoding VR-L may be cultured under conditions suitable for expression of their extracellular, transmembrane or intracellular domains and recovery of such peptides from cell culture. VR-L (or any of its domains) produced by a recombinant cell may be secreted or may be contained intracellularly, depending on the particular genetic construction used. In general, it is more convenient to prepare recombinant proteins in secreted form. Purification steps vary with the production process and the particular protein produced. Often an oligopeptide can be produced from a chimeric nucleotide sequence. This is accomplished by ligating the nucleotides from vr-l or a desired portion of the polypeptide to a nucleic acid sequence encoding a polypeptide domain which will facilitate protein purification (Kroll D J et al (1993) DNA Cell Biol 12:441–53).

In addition to recombinant production, fragments of VR-L may be produced by direct peptide synthesis using solid-phase techniques (eg Stewart et al (1969) Solid-Phase Peptide Synthesis, WH Freeman Co, San Francisco Calif.; Merrifield J (1963) J Am Chem Soc 85:2149–2154). Automated synthesis may be achieved, for example, using Applied Biosystems 431A Peptide Synthesizer (Foster City, Calif.) in accordance with the instructions provided by the manufacturer. Additionally, a particular portion of VR-L may be mutated during direct synthesis and combined with other parts of the peptide using chemical methods.

VR-L for antibody induction does not require biological activity; however, the protein must be antigenic. Peptides used to induce specific antibodies may have an aa sequence consisting of at least five aa, preferably at least 10 aa. They should mimic a portion of the aa sequence of the protein and may contain the entire aa sequence of a small naturally occurring molecule such as VR-L. An antigen portion of VR-L may be fused to another protein such as keyhole limpet hemocyanin, and the chimeric molecule used for antibody production.

Antibodies specific for VR-L may be produced by inoculation of an appropriate animal with the polypeptide or an antigenic fragment. An antibody is specific for VR-L if it is produced against an epitope of the polypeptide and binds to a least part of the natural or recombinant protein. Antibody production includes not only the stimulation of an immune response by injection into animals, but also analogous processes such as the production of synthetic antibodies, the screening of recombinant immunoglobulin libraries for specific-binding molecules (eg Orlandi R et al (1989) PNAS 86:3833–3837, or Huse W D et al (1989) Science 256: 1275–1281) or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules which specifically bind VR-L.

An additional embodiment of the subject invention is the use of VR-L specific antibodies, inhibitors or receptors as bioactive agents to treat pain.

Bioactive compositions comprising agonists, antagonists, receptors or inhibitors of VR-L may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems involving excessive lymphocyte and leukocyte trafficking.

The examples below are provided to illustrate the subject invention.

Identification of VR-L Receptor

The vr-l sequence of the present invention was identified in the partial sequences of two IMAGE clones (1286108 and 705190) among the sequences comprising a human tonsillar cell library enriched for germinal centre B cells. The enrichment was carried out by flow sorting (CD20+, IgD−). cDNA synthesis was primed with a NotI—oligo (dT) primer [5'-TGTTACCAATCTGAAGTGGGAGCGGC-CGCCTCATTTTTTTTTTTTTTT TTT-3'] (SEQ. ID. NO:3). Double stranded cDNA was ligated to Eco RI adaptors (Pharmacia), digested with NotI and cloned into the NotI and EcoRI sites of the modified pT7T3 vector. The library went through one round of normalisation.

Figure 3:
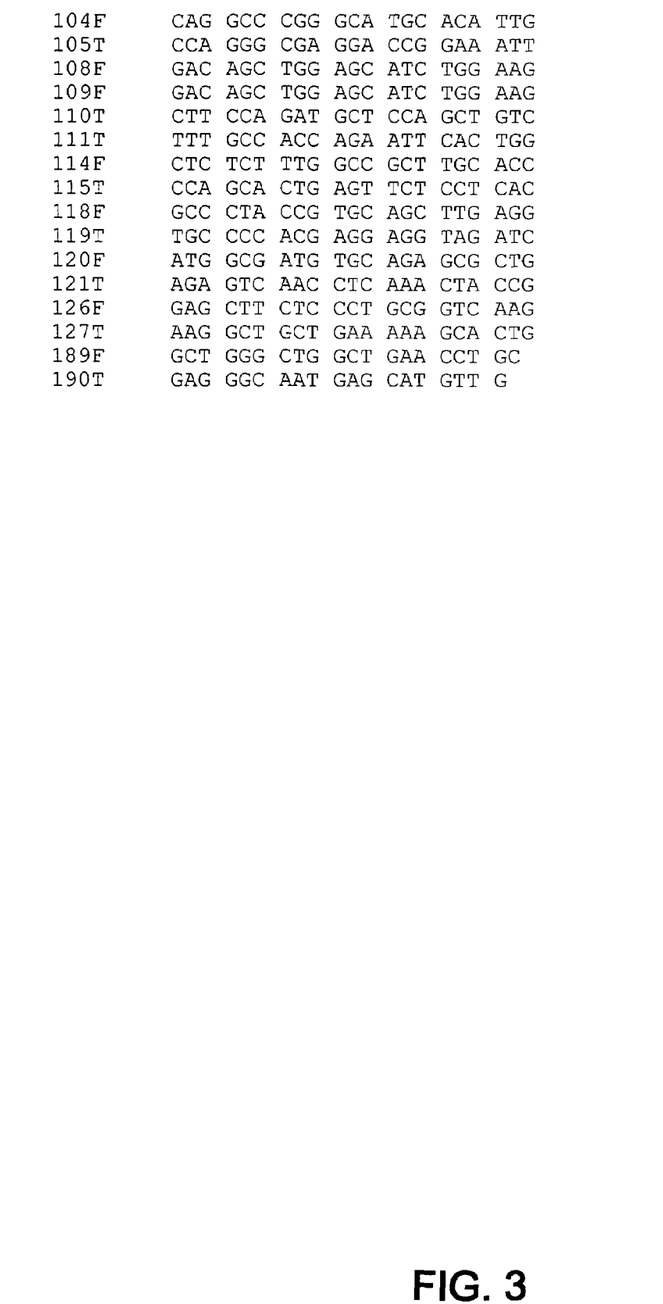
FIG. 3 shows the gene specific primers (SEQ ID NOS: 4–19) used to sequence the clones identified as forming part of the VR-L receptor. They are given as 5'-3' sequences with the F or T letter denoting whether they were specific for the target sequence in the 5'(F) or 3'(T) direction.

An EST database was searched using the blast (versions 1.4 and 2.0), fasta and Smith-Waterman algorithms with the rat VR1 DNA or protein sequence, and a number of human sequences with partial homology to VR1 were obtained. The cDNA clones used to derive these EST sequences were obtained from the IMAGE consortium and sequenced using the gene specific primers shown in FIG. 3 (SEQ ID NOS: 4–19).

Table I shows, by Genbank accession number, the identity of a number of human sequences with partial homology to VR1 thus identified.

TABLE 1

| H99578 | N24224 | N21167 | AA815110 |
|---|---|---|---|
| N21284 | AA357145 | AA814328 | H50364 |
| AA281348 | W38665 | H27879 | AA461295 |
| N35179 | N23395 | H49060 | H51393 |
| AA304033 | W44731 | H21490 | H20025 |
| T12251 | AA281349 | AA236417 | AA768829 |
| W92895 | AA236416 | N26729 | AA741232 |

Blast, which stands for Basic Local Alignment Search Tool, was used to search for local sequence alignments (Altschul et al (1997) Nucleic Acids Res. 25:3389–3402, Altschul et al (1993) J Mol Evol 36:290–300; Altschul, S F et al (1990) J Mol Biol 215:403–10). BLAST produces alignments of both nucleotide and aa sequences to determine sequence similarity. Because of the local nature of the alignments, blast is especially useful in determining exact matches or in identifying homologs. Whereas it is ideal for matches which do not contain gaps, it is inappropriate for performing motif-style searching. The fundamental unit of blast algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The blast approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Two cDNA clones (IMAGE clones 1286108 and 705190) were identified as together containing the entire coding region of the VR-L gene. DNA from these clones was digested with EcoRI (New England Biolabs) and the ends blunted by treatment with DNA Polymerase I (Klenow-Fragment, New England Biolabs) and dephosphorylated by treatment with Alkaline Phosphatase (calf-intestinal, Boehringer). The DNA was further digested with NotI (New England Biolabs). The resulting ~680 bp fragment from clone 1286108 and the ~1791 bp fragment from clone 705190 were purified and ligated using T4 DNA ligase. Ligation products corresponding to the ligation of 5'-1286108-3' to 5'-705190-3' (2471 bp) were purified and ligated into the mammalian expression vector pcDNA3.1Zeo+ (Invitrogen). Resultant clones were screened by restriction digest, and the insert completely sequenced on both strands (FIG. 1).

The tissue expression of the vr-l mRNA was determined by radioactive hybridisation of a random primed probe made from a 1346 bp region of the human vr-l cDNA (bases 735 to 2081) against poly (A)+ RNA isolated from a variety of human tissues, and supplied by Clontech (Human Master-Blot). The highest levels of specific hybridisation were found in lung, spleen, small intestine, thymus, placenta, and lymph node.

Functional Characterisation of the vr-l Gene Product

Methods

*Xenopus oocyte* Expression

Adult female *Xenopus laevis* were anaesthetized by immersion in a 0.4% solution of 3-aminobenzoic acid ethylester for 30–45 mins (or until unresponsive). Ovary tissue was removed via a small abdominal incision and Stage V and VI oocytes were isolated with fine forceps. After mild collagenase treatment to remove follicle cells (Type 1A, 0.5 mg mL$^{-1}$, for 8 mins), the oocyte nuclei were directly injected with 10–20 nl of injection buffer (88 mM NaCl, 1 mM KCl, 15 mM HEPES, at pH 7, filtered through nitrocellulose) or sterile water containing vr-l cDNA engineered into the expression vector pcDNA3.1Zeo. Following incubation for 48 hrs, oocytes were placed in a 50 μL bath and perfused at 4–6 mL min$^{-1}$ with modified Barth's medium (MBS) consisting of 88 mM NaCl, 1 mM KCl, 10 mM HEPES, 0.82 mM MgSO$_4$, 0.33 mM Ca(NO$_3$)$_2$, 0.91 mM CaCl$_2$, 2.4 mM NaHCO$_3$, at pH 7.5. Cells were impaled with two 1–3 MΩ electrodes containing 2 M KCl and voltage clamped between at −70 mV. Drugs were applied in the perfusate and heat was applied by bath applying preheated MBS.

Whole-Cell Patch Clamp

A glass coverslip containing a monolayer of human embryonic kidney (HEK) 293 cells transiently transfected with the vr-l cDNA was placed in a perspex chamber mounted on the stage of a Nikon Diaphot inverted phase-contrast microscope and continuously perfused with calcium-free artificial cerebrospinal fluid (aCSF, see below). Fire-polished patch pipettes were pulled on program 10 of a WZ, DMZ-Universal puller using conventional 120TF-10 electrode-glass. Pipette tip diameter was generally 1.5–2.5 μM, resistances were approximately 4MΩ. The intracellular pipette solution used is detailed below. High resistance (>10 GΩ) seals were formed by advancing the pipette onto the cell and exerting gentle suction to break through the membrane. The cells were voltage-clamped at −60 mV, using an Axon Axopatch 2 amplifier. Drugs or heated aCSF were applied to the cell under study by fast perfusion using a large internal diameter (50–100 μM) triple-barrel pipette assembly. Drug responses were obtained by rapidly positioning the perfusion pipette to completely envelop the cell in drug solution. This was achieved via a Biologic rapid solution changer which pivots the barrels into the desired position. Fast washout was obtained by re-positioning the washout barrel in line with the cell.

| Composition of calcium-free artificial cerebrospinal fluid (aCSF). | |
|---|---|
| NaCl | 149 mM |
| KCl | 3.25 mM |
| $MgCl_2$ | 2 mM |
| HEPES | 10 mM |
| D-Glucose | 11 mM |
| D(+)-Sucrose | 22 mM |
| pH 7.4 with NaOH | |

| Composition of caesium chloride intracellular pipette solution. | | | |
|---|---|---|---|
| Salt | Stock(M) | (mM) | ml/20 ml |
| CsCl | 1 | 130 | 2.6 |
| HEPES | 1 | 10 | 0.2 |
| BAPTA.Cs | | 10 | 200 mg |
| ATP.Mg | | 5 | 50.72 |
| Leupeptin | | 0.1 | 0.93 mg |
| $MgCl_2$ | 1 | 1 | 20 µl | pH = 7.3 320–340 mOsm

Results

Figure 2:
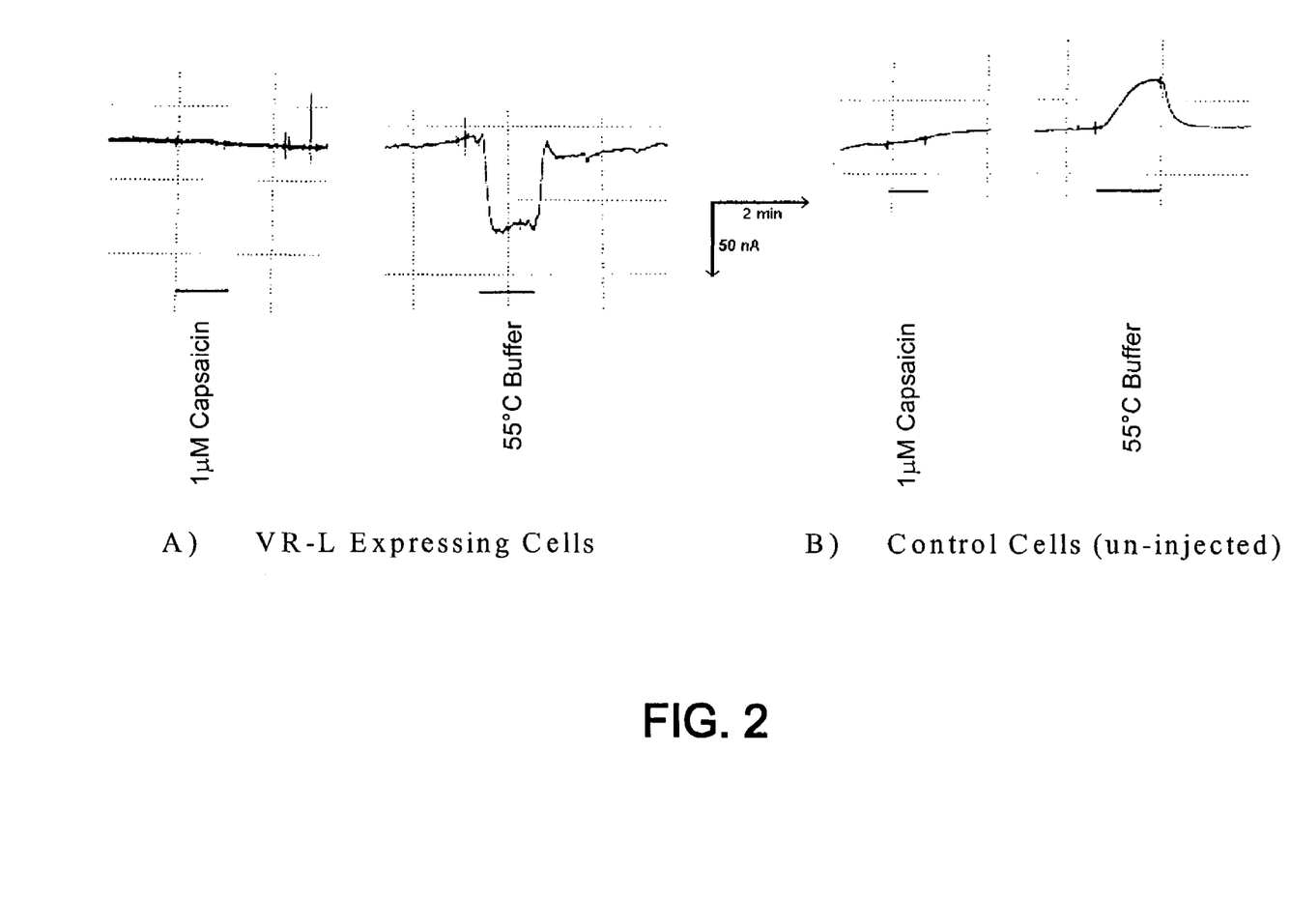
FIGS. 2A–2B show the effects of heat application and 1 µM capsaicin on ooctyes expressing (Panel A) and not expressing (Panel B) the receptors of the present application.

Human vr-l cDNA was expressed in *Xenopus* oocytes and in HEK 293 cells. In both expression systems inward currents were recorded to application of buffer warmed to 55° C., applied directly to the cell or via the bathing medium, which were not present in untransfected HEK cells or uninjected oocytes. No responses were produced by application of 1 µM capsaicin. FIG. 2 shows the effect of heat application and 1 µM capsaicin in (a) VR-L expressing oocytes and (b) control oocytes.

Knowledge of the correct, complete cDNA sequence of VR-L enables its use as a tool for antisense technology in the investigation of gene function. Oligonucleotides, cDNA or genomic fragments comprising the antisense strand of vr-l are used either in vitro or in vivo to inhibit expression of the mRNA. Such technology is now well known in the art, and antisense molecules can be designed at various locations along the nucleotide sequences. By treatment of cells or whole test animals with such antisense sequences, the gene of interest is effectively turned off. Frequently, the function of the gene is ascertained by observing behavior at the intracellular, cellular, tissue or organismal level (eg. lethality, loss of differentiated function, changes in morphology, etc.)

In addition to using sequences constructed to interrupt transcription of a particular open reading frame, modifications of gene expression are obtained by designing antisense sequences to intron regions, promoter/enhancer elements, or even to transacting regulatory genes. Similarly, inhibition is achieved using Hogeboom base-pairing methodology, also known as "triple helix" base pairing.

Two approaches are utilised to raise antibodies to VR-L and each approach is useful for generating either polyclonal or monoclonal antibodies. In one approach, denatured protein from reverse phase HPLC separation is obtained in quantities up to 75 mg. This denature protein is used to immunise mice or rabbits using standard protocols; about 100 µg are adequate for immunisation of a mouse, while up to 1 mg might be used to immunise a rabbit. For identifying mouse hybridomas, the denatured protein is radioiodinated and used to screen potential murine B-cell hybridomas for those which produce antibody. This procedure requires only small quantities of protein, such that 20 mg is sufficient for labelling and screening of several thousand clones.

In the second approach, the amino acid sequence of an appropriate VR-L domain, as deduced from translation of the cDNA, is analysed to determine regions of high antigenicity. Oligopeptides comprising appropriate hydrophilic regions are synthesised and used in suitable immunisation protocols to raise antibodies. Analysis to select appropriate epitopes is described by Ausubel F M et al (supra). The optimal amino acid sequences for immunisation are usually at the C-terminus, the N-terminus and those intervening, hydrophilic regions of the polypeptide which are likely to be exposed to the external environment when the protein is in its natural conformation.

Typically, selected peptides, about 15 residues in length, are synthesised using an Applied Biosystems Peptide Synthesiser Model 431A using fmoc-chemistry and coupled to keyhole limpet hemocyanin (KLH; Sigma, St Louis Mo.) by reaction with M-maleimidobenzoyl-N-hydroxysuccinimide ester (MBS; Ausubel F M et al, supra). If necessary, a cysteine is introduced at the N-terminus of the peptide to permit coupling to KLH. Rabbits are immunised with the peptide-KLH complex in complete Freund's adjuvant. The resulting antisera are tested for antipeptide activity by binding the peptide to plastic, blocking with 1% bovine serum albumin, reacting with antisera, washing and reacting with labelled (radioactive or fluorescent), affinity purified, specific goat anti-rabbit IgG.

Hybridomas are prepared and screened using standard techniques. Hybridomas of interest are detected by screening with labelled VR-L to identify those fusions producing the monoclonal antibody with the desired specificity. In a typical protocol, wells of plates (FAST; Becton-Dickinson, Palo Alto Calif.) are coated during incubation with affinity purified, specific rabbit anti-mouse (or suitable antispecies Ig) antibodies at 10 mg/ml. The coated wells are blocked with 1% BSA, washed and incubated with supernatants from hybridomas. After washing the wells are incubated with labelled VR-L at 1 mg/ml. Supernatants with specific antibodies bind more labelled VR-L than is detectable in the background. Then clones producing specific antibodies are expanded and subjected to two cycles of cloning at limiting dilution. Cloned hybridomas are grown in tissue culture by standard methods. Monoclonal antibodies with affinities of at least $10^8$ M-1, preferably $10^9$ to $10^{10}$ or stronger, are typically made by standard procedure as described in Harlow and Lane (1988) Antibodies: A Laboratory Manual, Cold Spring Harbor Laboratory, Cold Spring Harbor, N.Y.; and in Goding (1986) Monoclonal Antibodies: Principles and Practice, Academic Press, New York City.

Particular VR-L antibodies are useful for investigating signal transduction and the diagnosis of infectious or hereditary conditions which are characterised by differences in the amount or distribution of VR-L or downstream products of an active signalling cascade.

Diagnostic tests for VR-L include methods utilising an antibody and a label to detect VR-L in human body fluids, membranes, cells, tissues or extracts of such. The polypeptides and antibodies of the present invention are used with or without modification. Frequently, the polypeptides and antibodies are labelled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, chromogenic agents, magnetic particles and the like. Patents teaching the use of such lables include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567.

A variety of protocols for measuring soluble or membrane-bound VR-L, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilising monoclonal antibodies reactive to two non-interfering epitopes on VR-L is preferred, but a competitive binding assay may be employed. These assays are described, among other places, in Maddox, D E et al (1983, J Exp Med 158:1211f).

Native or recombinant VR-L is purified by immunoaffinity chromatography using antibodies specific for VR-L. In general, an immunoaffinity column is constructed by covalently coupling the anti-TRH antibody to an activated chromatographic resin.

Polyclonal immunoglobulins are prepared from immune sera either by precipitation with ammonium sulfate or by purification on immobilized Protein A (Pharmacia LKB Biotechnology, Piscataway N.J.). Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

A soluble VR-L containing preparation is passed over the immunoaffinity column, and the column is washed under conditions that allow the preferential absorbance of VR-L (eg. high ionic strength buffers in the presence of detergent). Then, the column is eluted under conditions that disrupt antibody/protein binding (eg. a buffer of pH 2–3 or a high concentration of a chaotrope such as urea or thiocyanate ion), and VR-L is collected.

This invention is particularly useful for screening therapeutic compounds by using VR-L or binding fragments thereof in any of a variety of drug screening techniques. The polypeptide or fragment employed in such a test is either free in solution, affixed to a solid support, borne on a cell surface or located intracellularly. One method of drug screening utilises eukaryotic or prokaryotic host cells which are stably transformed with recombinant nucleic acids expressing the polypeptide or fragment. Drugs are screened against such transformed cells in competitive binding assays. Such cells, either in viable or fixed form, are used for standard binding assays. One measures, for example, the formation of complexes between VR-L and the agent being tested. Alternatively, one examines the diminution in complex formation between VR-L and a receptor caused by the agent being tested.

Thus, the present invention provides methods of screening for drugs or any other agents which affect signal transduction. These methods, well known in the art, comprise contacting such a agent with VR-L polypeptide or a fragment thereof and assaying (i) for the presence of a complex between the agent and the VR-L polypeptide or fragment, or (ii) for the presence of a complex between the VR-L polypeptide or fragment and the cell. In such competitive binding assays, the VR-L polypeptide or fragment is typically labelled. After suitable incubation, free VR-L polypeptide or fragment is separated from the present in bound form, and the amount of free or uncomplexed label is a measure of the ability of the particular agent to bind to VR-L or to interfer with the VR-L and agent complex.

Another technique for drug screening provides high throughput screening for compounds having suitable binding affinity to the VR-L polypeptides and is described in detail in European Patent Application 84/03564, published on Sep. 13, 1984. Briefly stated, large numbers of different small peptide test compounds are synthesised on a solid substrate, such as plastic pins or some other surface. The peptide test compounds are reacted with VR-L polypeptide and washed. Bound VR-L polypeptide is then detected by methods well known in the art. Purified VR-L are also coated directly onto plates for use in the aforementioned drug screening techniques. In addition, non-neutralising antibodies are used to capture the peptide and immobilise it on the solid support.

This invention also contemplates the use of competitive drug screening assays in which neutralising antibodies capable of binding VR-L specifically compete with a test compound for binding to VR-L polypeptides or fragments thereof. In this manner, the antibodies are used to detect the presence of any peptide which shares one or more antigenic determinants with VR-L.

The goal of rational drug design is to produce structural analogues of biologically active polypeptides of interest or of small molecules with which they interact, agonists, antagonists, or inhibitors. Any of these examples are used to fashion drugs which are more active or stable forms of the polypeptide or which enhance or interfere with the function of a polypeptide in vivo (eg. Hodgson J (1991) Bio/Technology 9:19–21).

In one approach, the three-dimensional structure of a protein of interest, or of a protein-inhibitor complex, is determined by x-ray crystallography, by computer modelling or, most typically, by a combination of the two approaches. Both the shape and charges of the polypeptide must be ascertained to elucidate the structure and to determine active site(s) of the molecule. Less often, useful information regarding the structure of a polypeptide is gained by modelling based on the structure of homologous proteins. In both cases, relevant structural information is used to design efficient inhibitors. Useful examples of rational drug design includes molecules which have improved activity or stability as shown by Braxton S and Wells J A (1992, Biochemistry 31:7796–7801) or which act as inhibitors, agonists, or antagonists of native peptides as shown by Athauda S B et al (1993 J Biochem 113:742–46), incorporated herein by reference.

It is possible to isolate a target-specific antibody, selected by functional assay, as described above, and then to solve its crystal structure. This approach, in principle, yields a pharmacore upon which subsequent drug design is based. It is possible to bypass protein crystallography altogether by generating anti-idiotypic antibodies (anti-ids) to a functional, pharmacologically active antibody. As a mirror image of a mirror image, the binding site of the anti-ids is expected to be an analogue of the original receptor. The anti-id is then used to identify and isolate peptides from banks of chemically or biologically produced peptides. The isolated peptides then act as the pharmacore.

By virtue of the present invention, sufficient amount of polypeptide are made available to perform such analytical studies as X-ray crystallography. In addition, knowledge of the VR-L amino acid sequence provided herein provides guidance to those employing computer modelling techniques in place of or in addition to x-ray crystallography.

The inventive purified VR-L is a research tool for identification, characterisation and purification of interacting G or other signal transduction pathway proteins. Radioactive labels are incorporated into a selected VR-L domain by various methods known in the art and used in vitro to capture interacting molecules. A preferred method involves labelling the primary amino groups in VR-L with $^{125}$I Bolton-Hunter reagent (Bolton, A E and Hunter, W M (1973) Biochem J 133: 529). This reagent has been used to label various molecules without concomitant loss of biological activity (Hebert C A et al (1991) J Biol Chem 266: 18989; McColl S et al (1993) J Immunol 150:4550–4555).

Labeled VR-L is useful as a reagent for the purification of molecules with which it interacts. In one embodiment of affinity purification, membrane-bound VR-L is covalently coupled to a chromatography column. Cell-free extract derived from synovial cells or putative target cells is passed over the column, and molecules with appropriate affinity bind to VR-L. VR-L-complex is recovered from the column, and the VR-L-binding ligand disassociated and subjected to N-terminal protein sequencing. This aa sequence is then used to identify the captured molecule or to design degenerate oligonucleotide probes for cloning the relevant gene from an appropriate cDNA library.

In an alternate method, antibodies are raised against VR-L, specifically monoclonal antibodies. The monoclonal antibodies are screened to identify those which inhibit the binding of labelled VR-L. These monoclonal antibodies are then used therapeutically.

Antibodies, inhibitors, or antagonists of VR-L (or other treatments to limit signal transduction, LST) provide different effects when administered therapeutically. LSTs are formulated in a nontoxic, inert, pharmaceutically acceptable aqueous carrier medium preferably at a pH of about 5 to 8, more preferably 6 to 8, although pH may vary according to the characteristics of the antibody, inhibitor, or antagonist being formulated and the condition to be treated. Characteristics of LSTs include solubility of the molecule, half-life and antigenicity/immunogenicity. These and other characteristics aid in defining an effective carrier. Native human proteins are preferred as LSTs, but organic or synthetic molecules resulting from drug screens are equally effective in particular situations.

LSTs are delivered by known routes of administration including but not limited to topical creams and gels; transmucosal sprays and aerosols; transdermal patches and bandages; injectable, intravenous and lavage formulations; and orally administered liquids and pills particularly formulated to resist stomach acid and enzymes. The particular formulation, exact dosage, and route of administration is determined by the attending physician and varies according to each specific situation.

Such determinations are made by considering multiple variables such as the condition to be treated, the LST to be administered, and the pharmacokinetic profile of a particular LST. Additional factors which are taken into account include severity of the disease state, patient's age, weight, gender and diet, time and frequency of LST administration, possible combination with other drugs, reaction sensitivities, and tolerance/response to therapy. Long acting LST formulations might be administered every 3 to 4 days, every week, or once every two weeks depending on half-life and clearance rate of the particular LST.

Normal dosage amounts vary from 0.1 to 100,000 μg, up to a total dose of about 1 g, depending upon the route of administration. Guidance as to particular dosages and methods of delivery is provided in the literature; see U.S. Pat. Nos. 4,657,760; 5,206,344; or 5,225,212. Those skilled in the art employ different formulations for different LSTs. Administration to cells such as nerve cells necessitates delivery in a manner different from that to other cells such as vascular endothelial cells.

It is contemplated that abnormal signal transduction, trauma, or diseases which trigger VR-L activity are treatable with LSTs. These conditions or diseases are specifically diagnosed by the tests discussed above, and such testing should be performed in suspected cases of viral, bacterial or fungal infections; allergic responses; mechanical injury associated with trauma; hereditary diseases; lymphoma or carcinoma; or other conditions which activate the genes of lymphoid tissues.

SEQUENCE LISTING

```
<160> NUMBER OF SEQ ID NOS: 19

<210> SEQ ID NO 1
<211> LENGTH: 2469
<212> TYPE: DNA
<213> ORGANISM: Homo sapiens
<400> SEQUENCE: 1
cacgaggccg acgcgcagct gggaggaaga caggaccctt gacatctcca tctgcacaga     60
ggtcctggct ggaccgagca gcctcctcct cctaggatga cctcaccctc cagctctcca    120
gttttcaggt tggagacatt agatggaggc caagaagatg gctctgaggc ggacagagga    180
aagctggatt ttgggagcgg gctgcctccc atggagtcac agttccaggg cgaggaccgg    240
aaattcgccc ctcagataag agtcaacctc aactaccgaa agggaacagg tgccagtcag    300
ccggatccaa accgatttga ccgagatcgg ctcttcaatg cggtctcccg gggtgtcccc    360
gaggatctgg ctggacttcc agagtacctg agcaagacca gcaagtacct caccgactcg    420
```

-continued

```
gaatacacag agggctccac aggtaagacg tgcctgatga aggctgtgct gaaccttaag    480
gacggagtca atgcctgcat tctgccactg ctgcagatcg acagggactc tggcaatcct    540
cagcccctgg taaatgccca gtgcacagat gactattacc gaggccacag cgctctgcac    600
atcgccattg agaagaggag tctgcagtgt gtgaagctcc tggtggagaa tggggccaat    660
gtgcatgccc gggcctgcgg ccgcttcttc agaagggcc aagggacttg cttttatttc     720
ggtgagctac ccctctcttt ggccgcttgc accaagcagt gggatgtggt aagctacctc    780
ctggagaacc cacaccagcc cgccagcctg caggccactg actcccaggg caacacagtc    840
ctgcatgccc tagtgatgat ctcggacaac tcagctgaga acattgcact ggtgaccagc    900
atgtatgatg ggctcctcca agctggggcc cgcctctgcc ctaccgtgca gcttgaggac    960
atccgcaacc tgcaggatct cacgcctctg aagctggccg ccaaggaggg caagatcgag   1020
attttcaggc acatcctgca gcgggagttt caggactga gccacctttc ccgaaagttc    1080
accgagtggt gctatgggcc tgtccgggtg tcgctgtatg acctggcttc tgtggacagc   1140
tgtgaggaga actcagtgct ggagatcatt gcctttcatt gcaagagccc gcaccgacac   1200
cgaatggtcg ttttggagcc cctgaacaaa ctgctgcagg cgaaatggga tctgctcatc   1260
cccaagttct tcttaaactt cctgtgtaat ctgatctaca tgttcatctt caccgctgtt   1320
gcctaccatc agcctaccct gaagaagcag gccgcccctc acctgaaagc ggaggttgga   1380
aactccatgc tgctgacggg ccacatcctt atcctgctag gggggatcta cctcctcgtg   1440
ggccagctgt ggtacttctg gcggcgccac gtgttcatct ggatctcgtt catagacagc   1500
tactttgaaa tcctcttcct gttccaggcc ctgctcacag tggtgtccca ggtgctgtgt   1560
ttcctggcca tcgagtggta cctgccctg cttgtgtctg cgctggtgct gggctggctg    1620
aacctgcttt actatacacg tggcttccag cacacaggca tctacagtgt catgatccag   1680
aaggtcatcc tgcgggacct gctgcgcttc cttctgatct acttagtctt ccttttcggc   1740
ttcgctgtag ccctggtgag cctgagccag gaggcttggc gccccgaagc tcctacaggc   1800
cccaatgcca cagagtcagt gcagcccatg gagggacagg aggacgaggg caacggggcc   1860
cagtacaggg gtatcctgga agcctccttg gagctcttca aattcaccat cggcatgggc   1920
gagctggcct tccaggagca gctgcacttc gcgggcatgg tgctgctgct gctgctggcc   1980
tacgtgctgc tcacctacat cctgctgctc aacatgctca tcgccctcat gagcgagacc   2040
gtcaacagtg tcgccactga cagctggagc atctggaagc tgcagaaagc catctctgtc   2100
ctggagatgg agaatggcta ttggtggtgc aggaagaagc agcgggcagg tgtgatgctg   2160
accgttggca ctaagccaga tggcagcccg gatgagcgct ggtgcttcag ggtggaggag   2220
gtgaactggg cttcatggga gcagacgctg cctacgctgt gtgaggaccc gtcagggca    2280
ggtgtccctc gaactctcga gaaccctgtc ctggcttccc ctcccaagga ggatgaggat   2340
ggtgcctctg aggaaaacta tgtgcccgtc cagctcctcc agtccaactg atggcccaga   2400
tgcagcagga ggccagagga cagagcagag gatctttcca accacatctg ctggctctgg   2460
ggtcccagt                                                           2469
```

<210> SEQ ID NO 2
<211> LENGTH: 764
<212> TYPE: PRT
<213> ORGANISM: Homo sapiens

<400> SEQUENCE: 2

-continued

```
Met Thr Ser Pro Ser Ser Pro Val Phe Arg Leu Glu Thr Leu Asp
 1               5                  10                  15

Gly Gly Gln Glu Asp Gly Ser Glu Ala Asp Arg Gly Lys Leu Asp Phe
                20                  25                  30

Gly Ser Gly Leu Pro Pro Met Glu Ser Gln Phe Gln Gly Glu Asp Arg
            35                  40                  45

Lys Phe Ala Pro Gln Ile Arg Val Asn Leu Asn Tyr Arg Lys Gly Thr
 50                      55                  60

Gly Ala Ser Gln Pro Asp Pro Asn Arg Phe Asp Arg Asp Arg Leu Phe
 65                  70                  75                  80

Asn Ala Val Ser Arg Gly Val Pro Glu Asp Leu Ala Gly Leu Pro Glu
                85                  90                  95

Tyr Leu Ser Lys Thr Ser Lys Tyr Leu Thr Asp Ser Glu Tyr Thr Glu
                100                 105                 110

Gly Ser Thr Gly Lys Thr Cys Leu Met Lys Ala Val Leu Asn Leu Lys
            115                 120                 125

Asp Gly Val Asn Ala Cys Ile Leu Pro Leu Leu Gln Ile Asp Arg Asp
    130                 135                 140

Ser Gly Asn Pro Gln Pro Leu Val Asn Ala Gln Cys Thr Asp Asp Tyr
145                 150                 155                 160

Tyr Arg Gly His Ser Ala Leu His Ile Ala Ile Glu Lys Arg Ser Leu
                165                 170                 175

Gln Cys Val Lys Leu Leu Val Glu Asn Gly Ala Asn Val His Ala Arg
                180                 185                 190

Ala Cys Gly Arg Phe Phe Gln Lys Gly Gln Gly Thr Cys Phe Tyr Phe
            195                 200                 205

Gly Glu Leu Pro Leu Ser Leu Ala Ala Cys Thr Lys Gln Trp Asp Val
    210                 215                 220

Val Ser Tyr Leu Leu Glu Asn Pro His Gln Pro Ala Ser Leu Gln Ala
225                 230                 235                 240

Thr Asp Ser Gln Gly Asn Thr Val Leu His Ala Leu Val Met Ile Ser
                245                 250                 255

Asp Asn Ser Ala Glu Asn Ile Ala Leu Val Thr Ser Met Tyr Asp Gly
                260                 265                 270

Leu Leu Gln Ala Gly Ala Arg Leu Cys Pro Thr Val Gln Leu Glu Asp
            275                 280                 285

Ile Arg Asn Leu Gln Asp Leu Thr Pro Leu Lys Leu Ala Ala Lys Glu
    290                 295                 300

Gly Lys Ile Glu Ile Phe Arg His Ile Leu Gln Arg Glu Phe Ser Gly
305                 310                 315                 320

Leu Ser His Leu Ser Arg Lys Phe Thr Glu Trp Cys Tyr Gly Pro Val
                325                 330                 335

Arg Val Ser Leu Tyr Asp Leu Ala Ser Val Asp Ser Cys Glu Glu Asn
                340                 345                 350

Ser Val Leu Glu Ile Ile Ala Phe His Cys Lys Ser Pro His Arg His
            355                 360                 365

Arg Met Val Val Leu Glu Pro Leu Asn Lys Leu Leu Gln Ala Lys Trp
    370                 375                 380

Asp Leu Leu Ile Pro Lys Phe Phe Leu Asn Phe Leu Cys Asn Leu Ile
385                 390                 395                 400

Tyr Met Phe Ile Phe Thr Ala Val Ala Tyr His Gln Pro Thr Leu Lys
                405                 410                 415

Lys Gln Ala Ala Pro His Leu Lys Ala Glu Val Gly Asn Ser Met Leu
```

```
                420             425             430
Leu Thr Gly His Ile Leu Ile Leu Leu Gly Ile Tyr Leu Leu Val
            435             440             445
Gly Gln Leu Trp Tyr Phe Trp Arg Arg His Val Phe Ile Trp Ile Ser
        450             455             460
Phe Ile Asp Ser Tyr Phe Glu Ile Leu Phe Leu Phe Gln Ala Leu Leu
465             470             475             480
Thr Val Val Ser Gln Val Leu Cys Phe Leu Ala Ile Glu Trp Tyr Leu
                485             490             495
Pro Leu Leu Val Ser Ala Leu Val Leu Gly Trp Leu Asn Leu Leu Tyr
            500             505             510
Tyr Thr Arg Gly Phe Gln His Thr Gly Ile Tyr Ser Val Met Ile Gln
        515             520             525
Lys Val Ile Leu Arg Asp Leu Leu Arg Phe Leu Leu Ile Tyr Leu Val
            530             535             540
Phe Leu Phe Gly Phe Ala Val Ala Leu Val Ser Leu Ser Gln Glu Ala
545             550             555             560
Trp Arg Pro Glu Ala Pro Thr Gly Pro Asn Ala Thr Glu Ser Val Gln
                565             570             575
Pro Met Glu Gly Gln Glu Asp Glu Gly Asn Gly Ala Gln Tyr Arg Gly
            580             585             590
Ile Leu Glu Ala Ser Leu Glu Leu Phe Lys Phe Thr Ile Gly Met Gly
            595             600             605
Glu Leu Ala Phe Gln Glu Gln Leu His Phe Arg Gly Met Val Leu Leu
        610             615             620
Leu Leu Leu Ala Tyr Val Leu Leu Thr Tyr Ile Leu Leu Leu Asn Met
625             630             635             640
Leu Ile Ala Leu Met Ser Glu Thr Val Asn Ser Val Ala Thr Asp Ser
                645             650             655
Trp Ser Ile Trp Lys Leu Gln Lys Ala Ile Ser Val Leu Glu Met Glu
                660             665             670
Asn Gly Tyr Trp Trp Cys Arg Lys Lys Gln Arg Ala Gly Val Met Leu
            675             680             685
Thr Val Gly Thr Lys Pro Asp Gly Ser Pro Asp Glu Arg Trp Cys Phe
        690             695             700
Arg Val Glu Glu Val Asn Trp Ala Ser Trp Glu Gln Thr Leu Pro Thr
705             710             715             720
Leu Cys Glu Asp Pro Ser Gly Ala Gly Val Pro Arg Thr Leu Glu Asn
                725             730             735
Pro Val Leu Ala Ser Pro Pro Lys Glu Asp Glu Asp Gly Ala Ser Glu
            740             745             750
Glu Asn Tyr Val Pro Val Gln Leu Leu Gln Ser Asn
        755             760

<210> SEQ ID NO 3
<211> LENGTH: 51
<212> TYPE: DNA
<213> ORGANISM: Artificial Sequence
<220> FEATURE:
<223> OTHER INFORMATION: Primer

<400> SEQUENCE: 3
tgttaccaat ctgaagtggg agcggccgcc tcattttttt tttttttttt t            51

<210> SEQ ID NO 4
```

```
<211> LENGTH: 21
<212> TYPE: DNA
<213> ORGANISM: Artificial Sequence
<220> FEATURE:
<223> OTHER INFORMATION: PCR Primer

<400> SEQUENCE: 4
caggcccggg catgcacatt g                                              21

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
ccagggcgag gaccggaaat t                                              21

<210> SEQ ID NO 6
<211> LENGTH: 21
<212> TYPE: DNA
<213> ORGANISM: Artificial Sequence
<220> FEATURE:
<223> OTHER INFORMATION: PCR Primer

<400> SEQUENCE: 6
gacagctgga gcatctggaa g                                              21

<210> SEQ ID NO 7
<211> LENGTH: 21
<212> TYPE: DNA
<213> ORGANISM: Artificial Sequence
<220> FEATURE:
<223> OTHER INFORMATION: PCR Primer

<400> SEQUENCE: 7
gacagctgga gcatctggaa g                                              21

<210> SEQ ID NO 8
<211> LENGTH: 21
<212> TYPE: DNA
<213> ORGANISM: Artificial Sequence
<220> FEATURE:
<223> OTHER INFORMATION: PCR Primer

<400> SEQUENCE: 8
cttccagatg ctccagctgt c                                              21

<210> SEQ ID NO 9
<211> LENGTH: 21
<212> TYPE: DNA
<213> ORGANISM: Artificial Sequence
<220> FEATURE:
<223> OTHER INFORMATION: PCR Primer

<400> SEQUENCE: 9
tttgccacca gaattcactg g                                              21

<210> SEQ ID NO 10
<211> LENGTH: 21
<212> TYPE: DNA
<213> ORGANISM: Artificial Sequence
<220> FEATURE:
<223> OTHER INFORMATION: PCR Primer

<400> SEQUENCE: 10
```

```
ctctctttgg ccgcttgcac c                                          21

<210> SEQ ID NO 11
<211> LENGTH: 21
<212> TYPE: DNA
<213> ORGANISM: Artificial Sequence
<220> FEATURE:
<223> OTHER INFORMATION: PCR Primer

<400> SEQUENCE: 11
ccagcactga gttctcctca c                                          21

<210> SEQ ID NO 12
<211> LENGTH: 21
<212> TYPE: DNA
<213> ORGANISM: Artificial Sequence
<220> FEATURE:
<223> OTHER INFORMATION: PCR Primer

<400> SEQUENCE: 12
gccctaccgt gcagcttgag g                                          21

<210> SEQ ID NO 13
<211> LENGTH: 21
<212> TYPE: DNA
<213> ORGANISM: Artificial Sequence
<220> FEATURE:
<223> OTHER INFORMATION: PCR Primer

<400> SEQUENCE: 13
tgccccacga ggaggtagat c                                          21

<210> SEQ ID NO 14
<211> LENGTH: 21
<212> TYPE: DNA
<213> ORGANISM: Artificial Sequence
<220> FEATURE:
<223> OTHER INFORMATION: PCR Primer

<400> SEQUENCE: 14
atggcgatgt gcagagcgct g                                          21

<210> SEQ ID NO 15
<211> LENGTH: 21
<212> TYPE: DNA
<213> ORGANISM: Artificial Sequence
<220> FEATURE:
<223> OTHER INFORMATION: PCR Primer

<400> SEQUENCE: 15
agagtcaacc tcaaactacc g                                          21

<210> SEQ ID NO 16
<211> LENGTH: 21
<212> TYPE: DNA
<213> ORGANISM: Artificial Sequence
<220> FEATURE:
<223> OTHER INFORMATION: PCR Primer

<400> SEQUENCE: 16
gagcttctcc ctgcggtcaa g                                          21

<210> SEQ ID NO 17
<211> LENGTH: 21
<212> TYPE: DNA
```

-continued

```
<213> ORGANISM: Artificial Sequence
<220> FEATURE:
<223> OTHER INFORMATION: PCR Primer

<400> SEQUENCE: 17
aaggctgctg aaaaagcact g                                              21

<210> SEQ ID NO 18
<211> LENGTH: 20
<212> TYPE: DNA
<213> ORGANISM: Artificial Sequence
<220> FEATURE:
<223> OTHER INFORMATION: PCR Primer

<400> SEQUENCE: 18
gctgggctgg ctgaacctgc                                                20

<210> SEQ ID NO 19
<211> LENGTH: 19
<212> TYPE: DNA
<213> ORGANISM: Artificial Sequence
<220> FEATURE:
<223> OTHER INFORMATION: PCR Primer

<400> SEQUENCE: 19
gagggcaatg agcatgttg                                                 19
```

The invention claimed is:

1. An isolated polynucleotide consisting of a nucleic acid sequence encoding the polypeptide of SEQ ID NO: 2, or the complement of said polynucleotide.

2. An isolated polynucleotide comprising the nucleic acid sequence of SEQ ID NO: 1.

3. An isolated polynucleotide comprising the complement of the polynucleotide sequence provided in SEQ ID NO: 1.

4. An expression vector comprising the polynucleotide of claim 1.

5. An isolated host cell transformed with the expression vector of claim 4.

6. A method of producing a polypeptide, said method comprising the steps of:
   a) culturing the host cell of claim 5 under conditions suitable for the expression of the polypeptide; and
   b) recovering the polypeptide from the host cell culture.

* * * * *